US012718960B2

(12) United States Patent
Scavo et al.

(10) Patent No.: US 12,718,960 B2
(45) Date of Patent: Aug. 25, 2026

(54) SYSTEMS, METHODS, AND APPARATUSES FOR DETERMINING A DRUG SHORTAGE IN AN ELECTRONIC ENVIRONMENT

(71) Applicant: Premier Healthcare Solutions, Inc., Charlotte, NC (US)

(72) Inventors: Shelley Parks Scavo, Davidson, NC (US); Jill Christy Jenkins, Clover, SC (US); Nichole Ann Walton Barnes, Maysville, NC (US); Jessica Lynne Daley, Mars, PA (US); Paula Gurz, Lake Wylie, SC (US); Patrick Michael Sudol, Fort Mill, SC (US); Sudha Narayanaswamy, Plainsboro, NJ (US)

(73) Assignee: PREMIER HEALTHCARE SOLUTIONS, INC., Charlotte, NC (US)

( * ) Notice: Subject to any disclaimer, the term of this patent is extended or adjusted under 35 U.S.C. 154(b) by 20 days.

(21) Appl. No.: 18/620,442

(22) Filed: Mar. 28, 2024

(65) Prior Publication Data

US 2024/0347214 A1 Oct. 17, 2024

Related U.S. Application Data

(60) Provisional application No. 63/455,507, filed on Mar. 29, 2023.

(51) Int. Cl.
*G16H 70/40* (2018.01)
*G06Q 30/0202* (2023.01)

(52) U.S. Cl.
CPC ......... *G16H 70/40* (2018.01); *G06Q 30/0202* (2013.01)

(58) Field of Classification Search
None
See application file for complete search history.

(56) References Cited

U.S. PATENT DOCUMENTS

| | | | | |
|---|---|---|---|---|
| 2014/0222593 | A1* | 8/2014 | Cosman | G06Q 30/0264 705/14.73 |
| 2018/0197128 | A1* | 7/2018 | Carstens | G06F 16/9024 |
| 2020/0074402 | A1* | 3/2020 | Adato | G06V 20/52 |
| 2020/0210947 | A1* | 7/2020 | Devarakonda | G06Q 10/06312 |
| 2020/0320470 | A1* | 10/2020 | Whitney | G06F 9/547 |

OTHER PUBLICATIONS

Abu Zwaida et al. (âOptimization of inventory management to prevent drug shortages in the hospital supply chain.â Applied Sciences Nov. 6 (2021)) (Year: 2021).*

* cited by examiner

*Primary Examiner* — Christopher B Tokarczyk
(74) *Attorney, Agent, or Firm* — Moore & Van Allen PLLC

(57) ABSTRACT

Systems, methods, and apparatuses are described herein for determining a drug shortage in an electronic environment. The present invention is configured to identify at least one drug identifier; identify at least one route type for the at least one drug resource identifier; determine at least one feature type associated with the at least one drug identifier, wherein each feature type comprises at least one attribute; generate a shortage score for the drug identifier; apply a post-score change to the shortage score, wherein the post-score change is based on at least one supplemental feature; and generate a drug shortage score based on the post-score change applied to the shortage score.

20 Claims, 8 Drawing Sheets

DETERMINE A ROUTE TYPE FROM THE AT LEAST ONE ROUTE TYPE FOR THE AT LEAST ONE DRUG IDENTIFIER, WHEREIN THE ROUTE TYPE IS USED TO GENERATE THE SHORTAGE SCORE FOR THE DRUG IDENTIFIER
402

SYSTEMS, METHODS, AND APPARATUSES FOR DETERMINING A DRUG SHORTAGE IN AN ELECTRONIC ENVIRONMENT

CROSS-REFERENCE TO RELATED APPLICATIONS

This application claims the benefit of U.S. Provisional Patent Application No. 63/455,507, filed Mar. 29, 2023, entitled "SYSTEMS, METHODS, AND APPARATUSES FOR DETERMINING A DRUG SHORTAGE IN AN ELECTRONIC ENVIRONMENT", the entirety of which is incorporated herein by reference.

FIELD OF INVENTION

The present invention embraces a system for determining a drug shortage in an electronic environment.

BACKGROUND

Recipients of products and resources that are critical to their day-to-day organizations may have a harder time than ever predicting when a resource or product shortage may occur. Further, and in certain industries—such as prescription and drug industries, including industries associated with the national drug codes (NDCs) and the federal drug administration (FDA)—drug shortages need to be determined before the shortage happens. Thus, there exists a need for a system that can accurately, efficiently, and dynamically determine future, potential drug shortages.

SUMMARY

The following presents a simplified summary of one or more embodiments of the present invention, in order to provide a basic understanding of such embodiments. This summary is not an extensive overview of all contemplated embodiments and is intended to neither identify key or critical elements of all embodiments nor delineate the scope of any or all embodiments. Its sole purpose is to present some concepts of one or more embodiments of the present invention in a simplified form as a prelude to the more detailed description that is presented later.

In one aspect, a system for determining a drug shortage is provided. In some embodiments, the system may comprise a memory device with computer-readable program code stored thereon; at least one processing device operatively coupled to the at least one memory device and the at least one communication device, wherein executing the computer-readable code is configured to cause the at least one processing device to: identify at least one drug identifier; identify at least one route type for the at least one drug resource identifier; determine at least one feature type associated with the at least one drug identifier, wherein each feature type comprises at least one attribute; generate a shortage score for the drug identifier; apply a post-score change to the shortage score, wherein the post-score change is based on at least one supplemental feature; and generate a drug shortage score based on the post-score change applied to the shortage score.

In some embodiments, the processing device is further configured to identify data associated with the at least one drug identifier from at least one resource statement; apply a drug shortage model to the data associated with the at least one drug identifier; determine, based on the drug shortage model, the at least one feature type; and generate, based on the drug shortage model, the drug shortage score.

In some embodiments, the processing device is further configured to determine a route type from the at least one route type for the at least one drug identifier, wherein the route type is used to generate the shortage score for the drug identifier.

In some embodiments, the processing device if further configured to rank each drug shortage score for each drug identifier in a route-type rank, wherein the route-type rank comprises the drug shortage score for each drug identifier associated with a same route type. In some embodiments, the processing device if further configured to: generate a drug-route shortage graphical user interface, wherein the drug-route shortage graphical user interface comprises the at least one drug shortage scores of a route-type that meets a drug-route shortage threshold, wherein, in the instance where the route-type is less than the drug-route shortage threshold, generate the drug-route shortage graphical user interface to indicate a pre-determined percentage of a top drug shortage scores, or wherein, in an instance where the route-type meets the drug-route shortage threshold, generate the drug-route shortage graphical user interface to indicate the drug-route shortage threshold of the top drug shortage scores.

In some embodiments, the processing is further configured to: identify data associated with the at least one drug identifier from at least one resource statement; filter the data associated with the at least one drug identifier to generate filtered drug data of the at least one drug identifier; and apply the filtered drug data to the at least one attribute of each feature type to generate the shortage score.

In some embodiments, the at least one route type comprises at least one of an injection route, an oral route, a topical route, an intravenous route, an intramuscular route, a subcutaneous route, a rectal route, a vaginal route, an inhaled route, an ocular route, or an optic route.

In some embodiments, the at least one attribute comprises at least one of a fixed drug feature, a shortage event feature, a changing drug feature, a line-item feature, or a relatedness feature.

In some embodiments, shortage score is an aggregate of each attribute associated with each feature type.

In some embodiments, the at least one supplemental feature comprises an increase or decrease to the shortage score based on at least one of a previous supply trend for the drug identifier, a current supply trend, the route type, a supply trend of units, or a backorder trend.

In some embodiments, the drug shortage score is generated at a weekly rate.

In another aspect, a computer program product for determining a drug shortage is provided. In some embodiments, the computer program product comprises at least one non-transitory computer-readable medium having computer-readable program code portions embodied therein, the computer-readable program code portions which when executed by a processing device are configured to cause the processor to: identify at least one drug identifier; identify at least one route type for the at least one drug resource identifier; determine at least one feature type associated with the at least one drug identifier, wherein each feature type comprises at least one attribute; generate a shortage score for the drug identifier; apply a post-score change to the shortage score, wherein the post-score change is based on at least one supplemental feature; and generate a drug shortage score based on the post-score change applied to the shortage score.

In some embodiments, the processing device is further configured to cause the processor to: identify data associated with the at least one drug identifier from at least one resource statement; apply a drug shortage model to the data associated with the at least one drug identifier; determine, based on the drug shortage model, the at least one feature type; and generate, based on the drug shortage model, the drug shortage score.

In some embodiments, the processing device is further configured to cause the processor to: determine a route type from the at least one route type for the at least one drug identifier, wherein the route type is used to generate the shortage score for the drug identifier.

In some embodiments, the processing device is further configured to cause the processor to: rank each drug shortage score for each drug identifier in a route-type rank, wherein the route-type rank comprises the drug shortage score for each drug identifier associated with a same route type. In some embodiments, the processing device is further configured to cause the processor to: generate a drug-route shortage graphical user interface, wherein the drug-route shortage graphical user interface comprises the at least one drug shortage scores of a route-type that meets a drug-route shortage threshold, wherein, in the instance where the route-type is less than the drug-route shortage threshold, generate the drug-route shortage graphical user interface to indicate a pre-determined percentage of a top drug shortage scores, or wherein, in an instance where the route-type meets the drug-route shortage threshold, generate the drug-route shortage graphical user interface to indicate the drug-route shortage threshold of the top drug shortage scores.

In another aspect, a computer implemented method for determining a drug shortage is provided. In some embodiments, the computer-implemented method comprises: identifying at least one drug identifier; identifying at least one route type for the at least one drug resource identifier; determining at least one feature type associated with the at least one drug identifier, wherein each feature type comprises at least one attribute; generating a shortage score for the drug identifier; applying a post-score change to the shortage score, wherein the post-score change is based on at least one supplemental feature; and generating a drug shortage score based on the post-score change applied to the shortage score.

In some embodiments, the computer-implemented method further comprises: identifying data associated with the at least one drug identifier from at least one resource statement; applying a drug shortage model to the data associated with the at least one drug identifier; determining, based on the drug shortage model, the at least one feature type; and generating, based on the drug shortage model, the drug shortage score.

In some embodiments, the computer-implemented method further comprises: determining a route type from the at least one route type for the at least one drug identifier, wherein the route type is used to generate the shortage score for the drug identifier.

In some embodiments, the computer-implemented method further comprises: ranking each drug shortage score for each drug identifier in a route-type rank, wherein the route-type rank comprises the drug shortage score for each drug identifier associated with a same route type.

As will be understood by one of ordinary skill in the art, the above-recited features may also be implemented at least by a computer-implemented method, a computer-program product, and/or the like.

BRIEF DESCRIPTION OF THE DRAWINGS

Figure 1A:
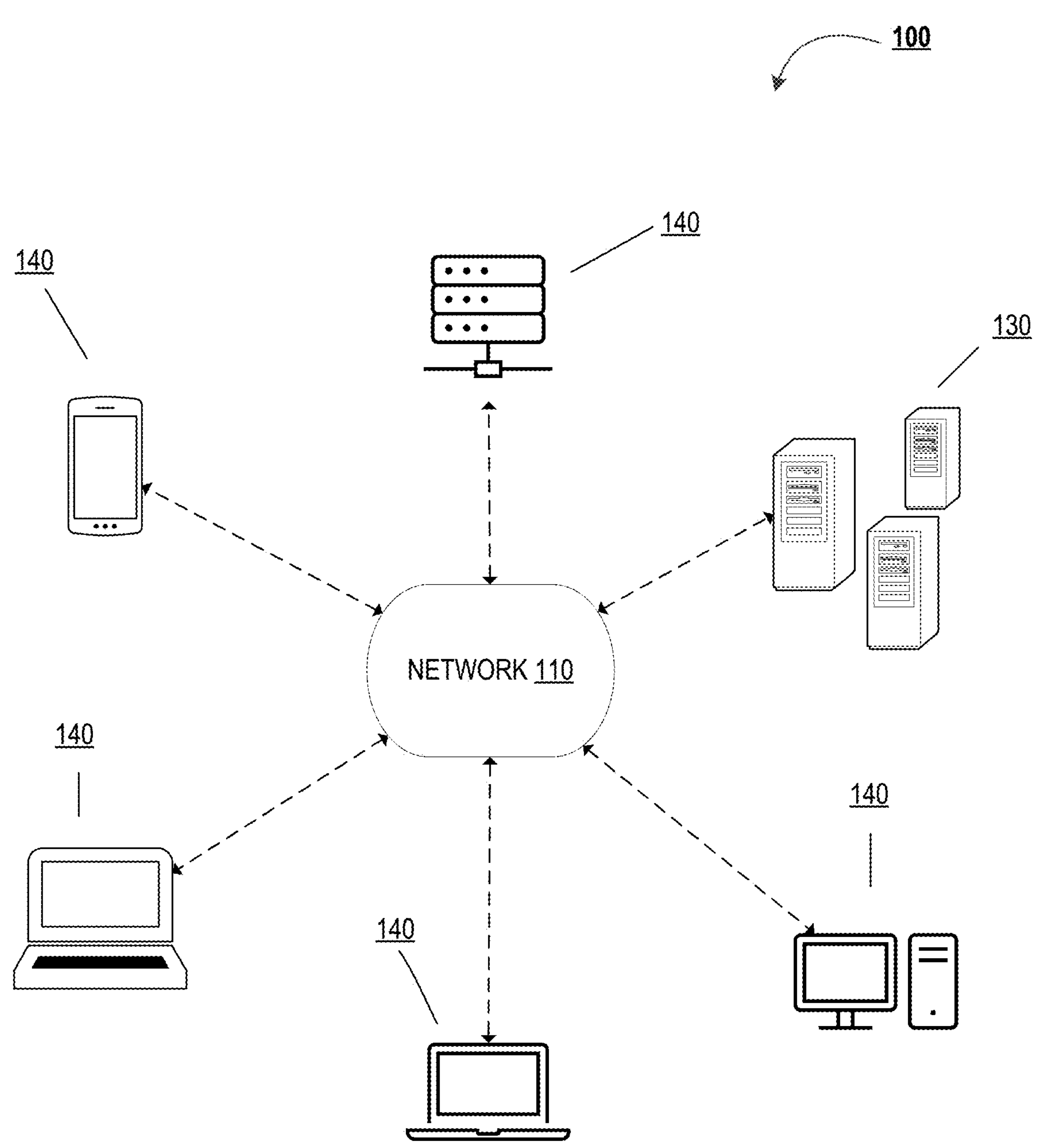
Figure 1B:
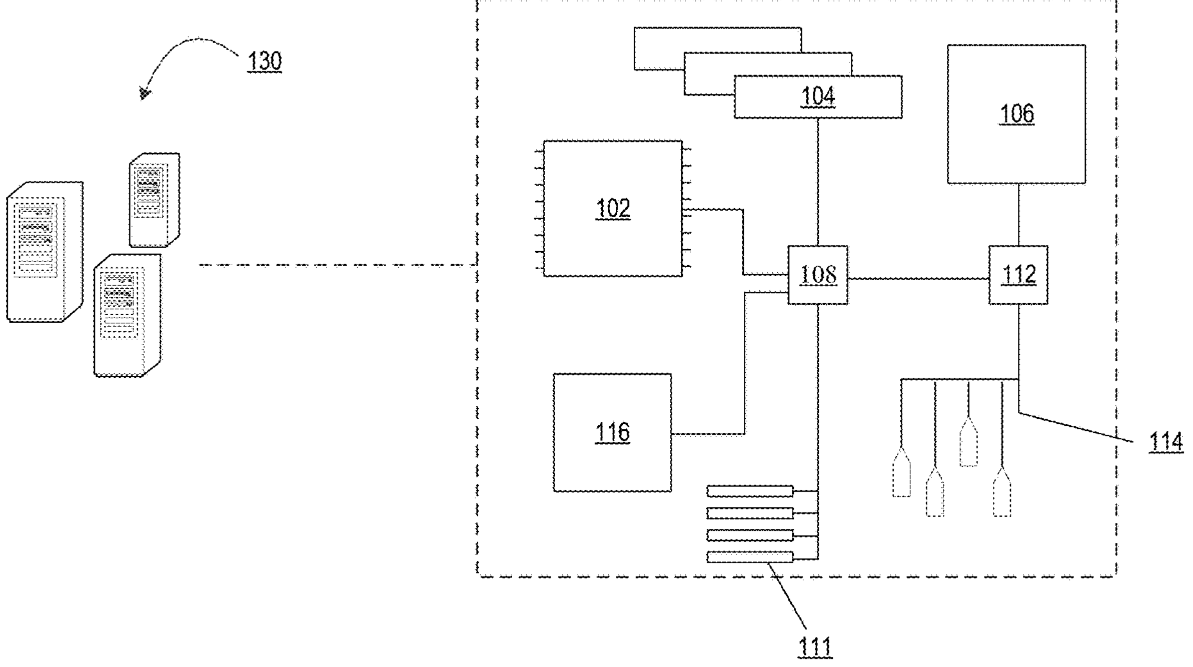
Figure 1C:
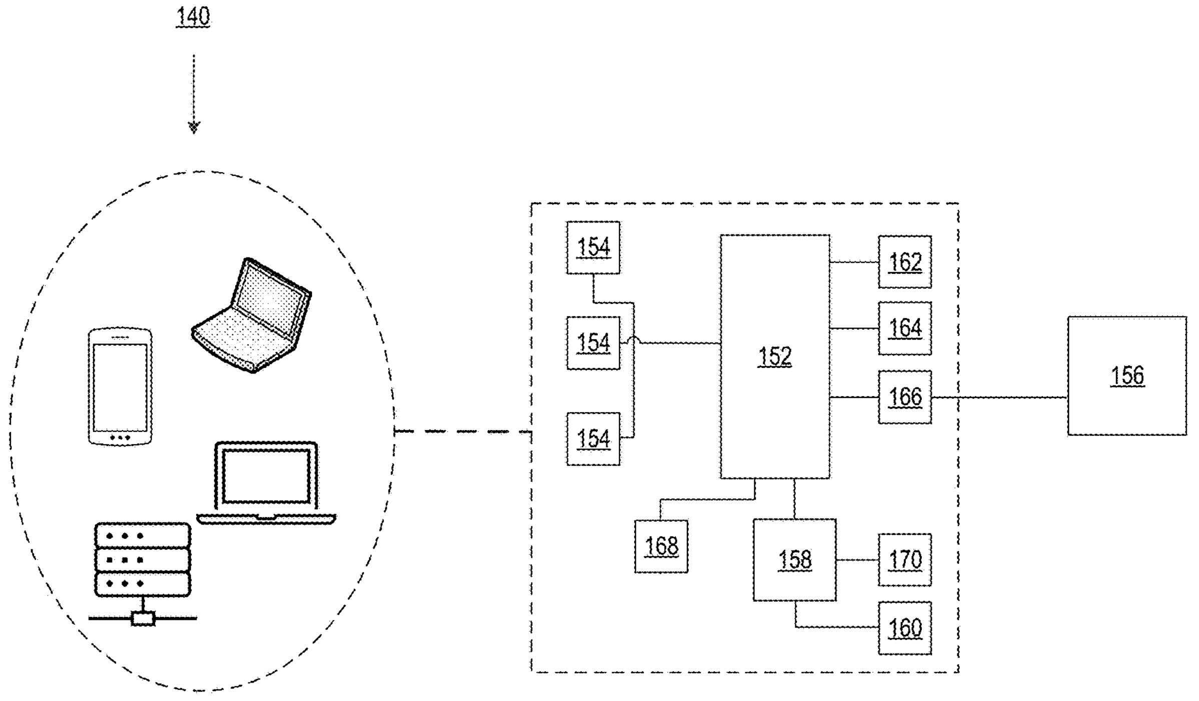
Figure 2:
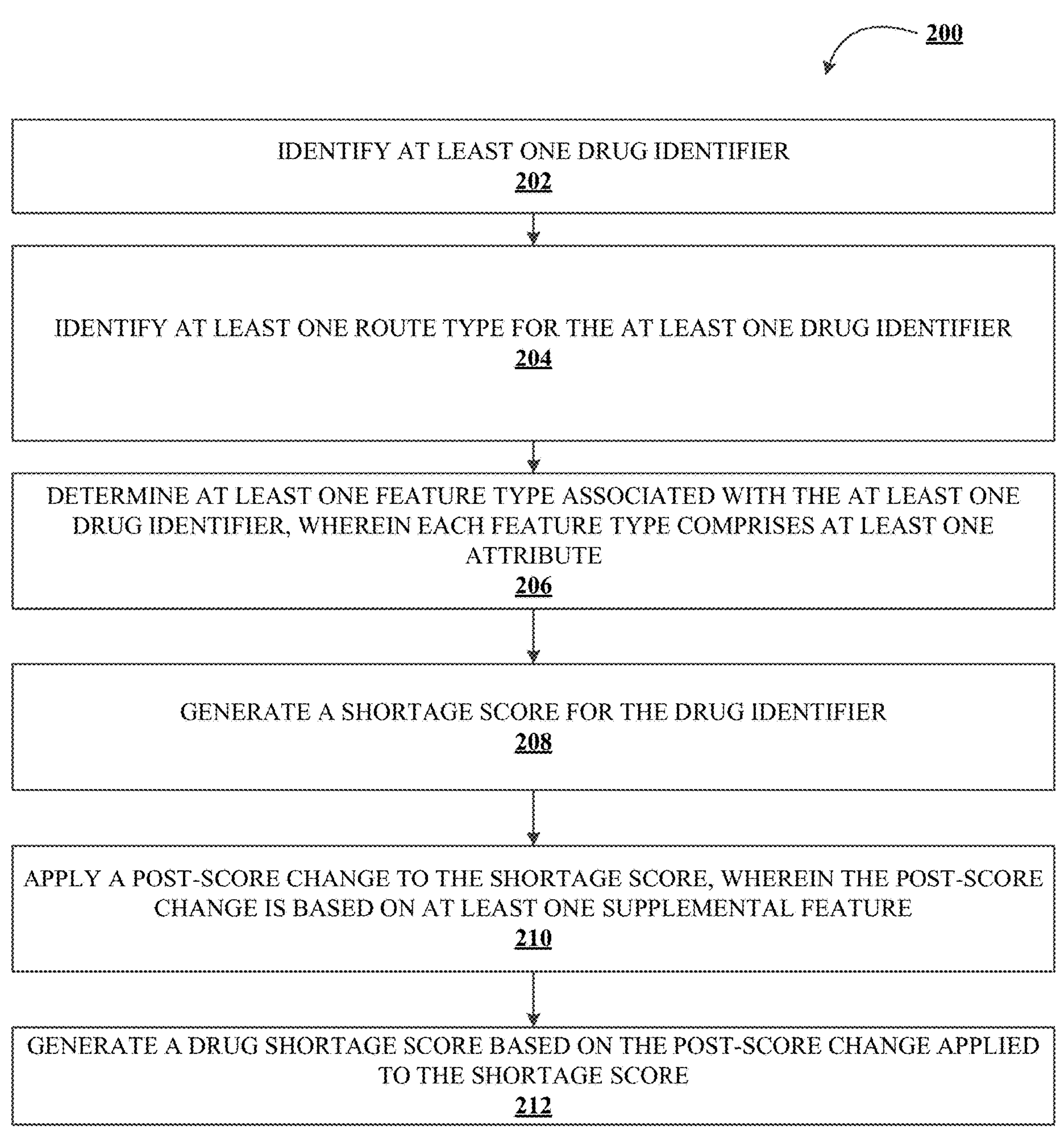
Figure 3:
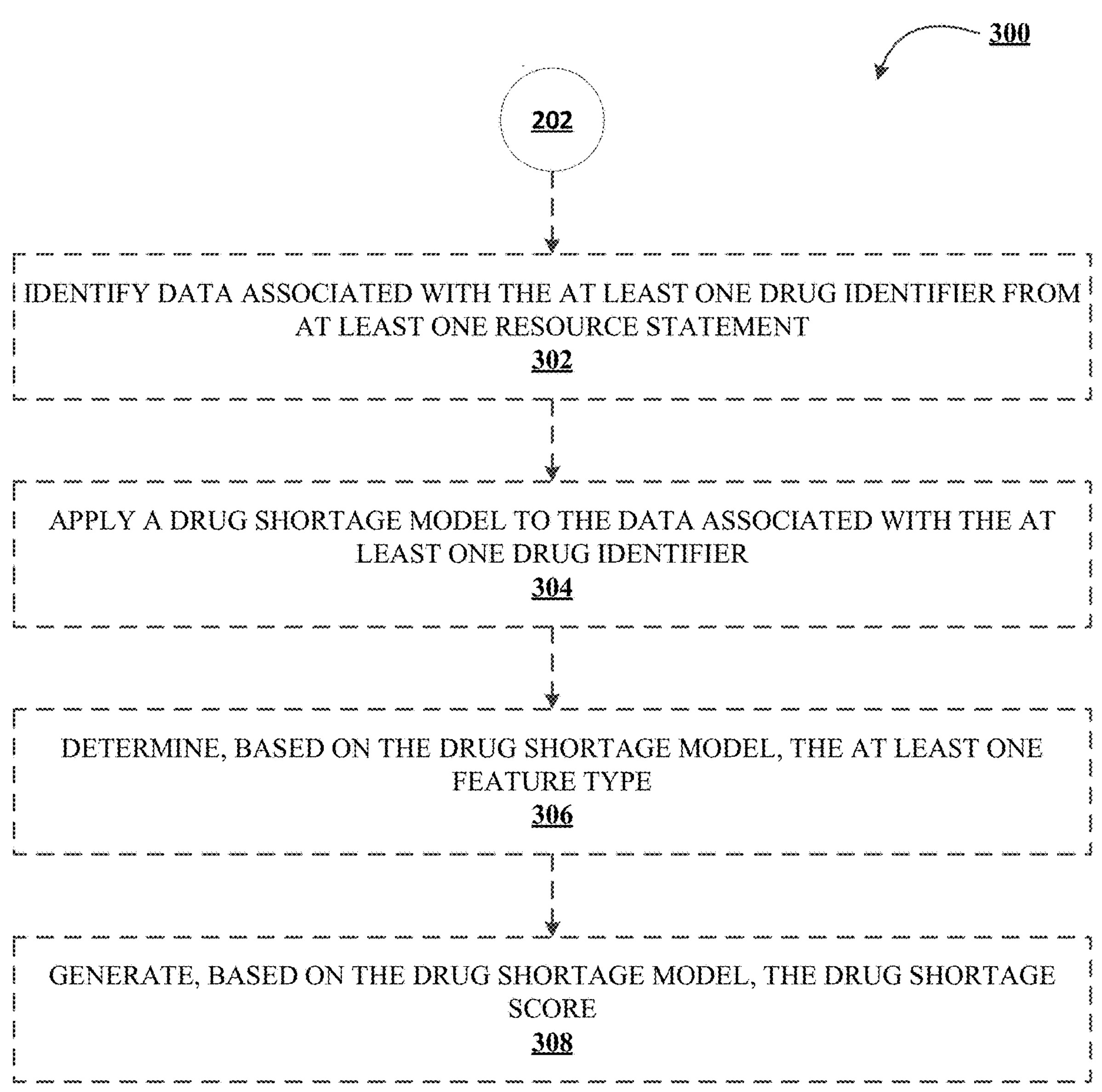
Figure 4:
Figure 4:
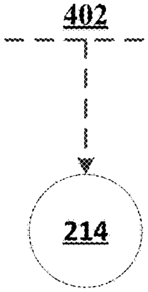
Figure 5:
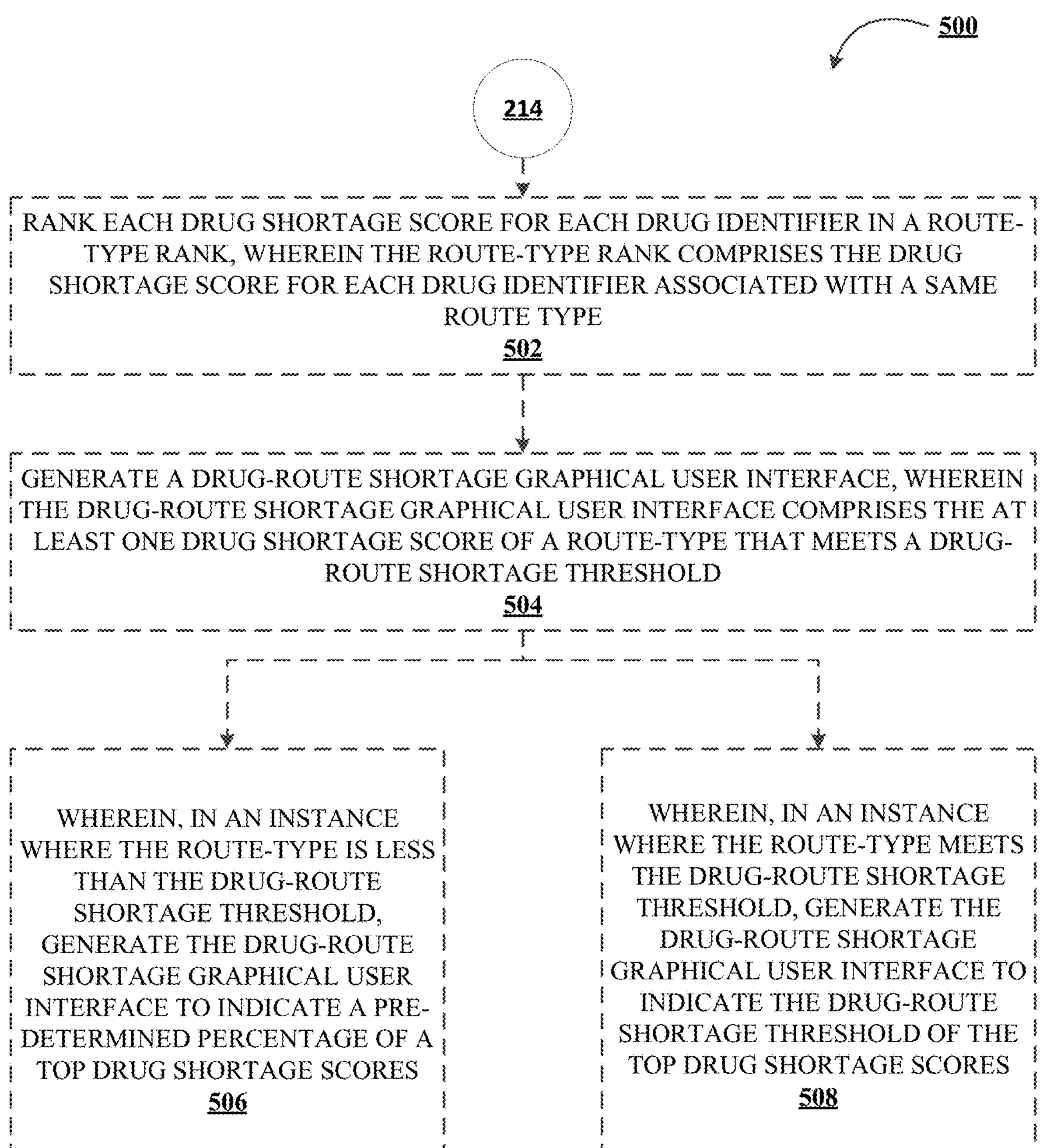
Figure 6:
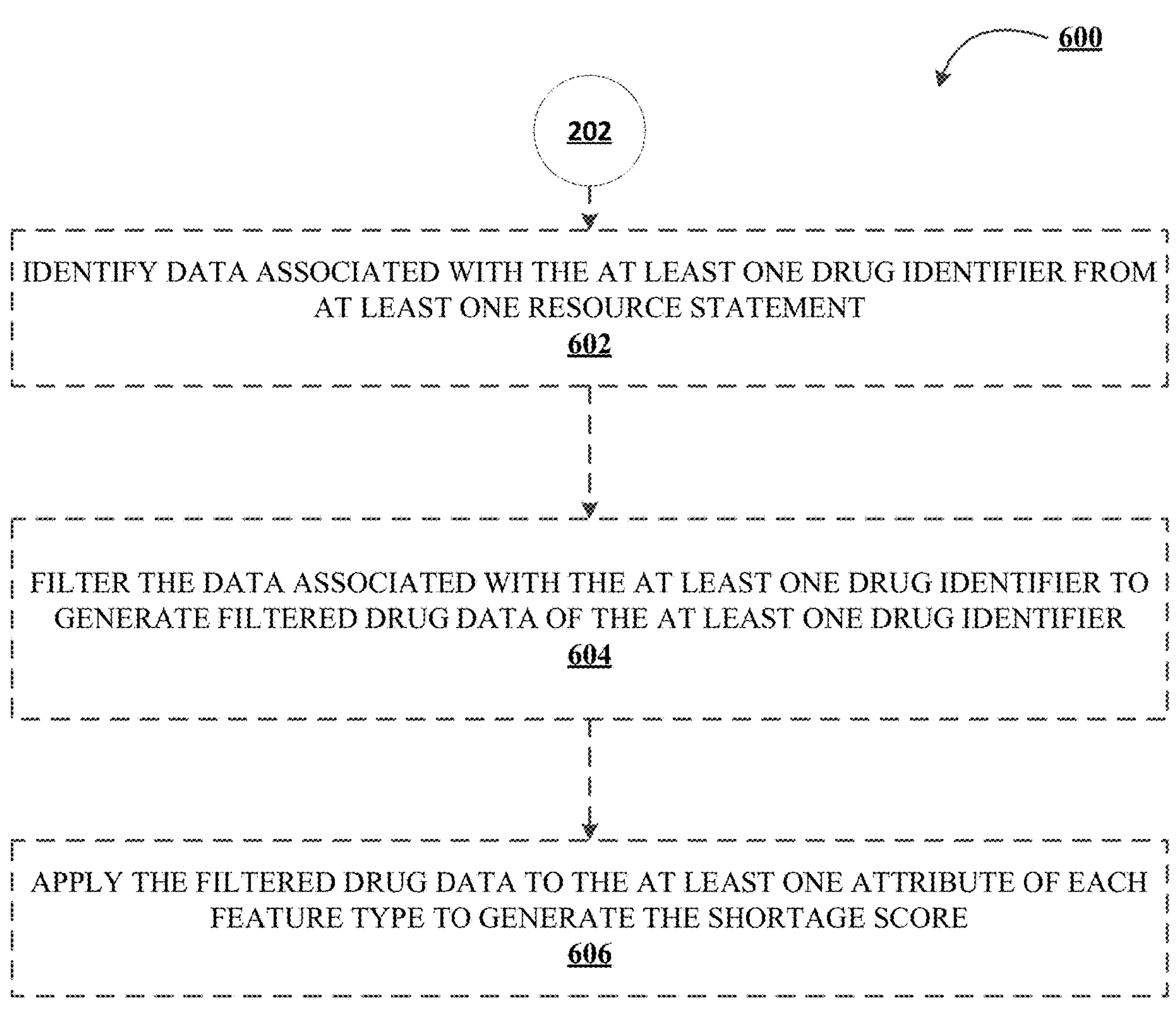

Having thus described embodiments of the invention in general terms, reference will now be made to the accompanying drawings, wherein:

FIGS. 1A-1C illustrates technical components of an exemplary distributed computing environment for determining a drug shortage, in accordance with an embodiment of the invention;

FIG. 2 illustrates an exemplary process flow for determining a drug shortage, in accordance with an embodiment of the disclosure;

FIG. 3 illustrates an exemplary process flow for generating a drug shortage score, in accordance with an embodiment of the disclosure;

FIG. 4 illustrates an exemplary process flow for determining a route type for the drug identifier(s) and using the route type to generate the shortage score for each drug identifier, in accordance with an embodiment of the disclosure;

FIG. 5 illustrates an exemplary process flow for generating a drug-route shortage graphical user interface, in accordance with an embodiment of the disclosure; and FIG. 6 illustrates an exemplary process flow for generating the shortage score, in accordance with an embodiment of the disclosure.

DETAILED DESCRIPTION OF EMBODIMENTS OF THE INVENTION

Embodiments of the present invention will now be described more fully hereinafter, with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Where possible, any terms expressed in singular form herein are meant to also include the plural form and vice versa, unless explicitly stated otherwise. Also, as used herein, the term "a" and/or "an" shall mean "one or more," even though the phrase "one or more" is also used herein. Furthermore, when it is said herein that something is "based on" something else, it may be based on one or more other things as well. In other words, unless expressly indicated otherwise, as used herein "based on" means "based at least in part on" or "based at least partially on." Like numbers refer to like elements throughout.

FIGS. 1A-1C illustrate technical components of an exemplary distributed computing environment for determining a drug shortage 100, in accordance with an embodiment of the invention. As shown in FIG. 1A, the distributed computing environment 100 contemplated herein may include a system 130, a client device(s) 140, and a network 110 over which the system 130 and client device(s) 140 communicate therebetween. FIG. 1A illustrates only one example of an embodiment of the distributed computing environment 100, and it will be appreciated that in other embodiments one or more of the systems, devices, and/or servers may be combined into a single system, device, or server, or be made up of multiple systems, devices, or servers. Also, the distributed computing environment 100 may include multiple systems, same or similar to system 130, with each system providing portions of the necessary operations (e.g., as a server bank, a group of blade servers, or a multi-processor system).

In some embodiments, the system 130 and the client device(s) 140 may have a client-server relationship in which the client device(s) 140 are remote devices that request and receive service from a centralized server, i.e., the system 130. In some other embodiments, the system 130 and the client device(s) 140 may have a peer-to-peer relationship in which the system 140 and the client device(s) 140 are considered equal and all have the same abilities to use the resources available on the network 110. Instead of having a central server (e.g., system 130) which would act as the shared drive, each device that is connected to the network 110 would act as the server for the files stored on it.

The system 130 may represent various forms of servers, such as web servers, database servers, file server, or the like, various forms of digital computing devices, such as laptops, desktops, video recorders, audio/video players, radios, workstations, or the like, or any other auxiliary network devices, such as wearable devices, Internet-of-things devices, electronic kiosk devices, mainframes, or the like, or any combination of the aforementioned.

The client device(s) 140 may represent various forms of electronic devices, including user input devices such as personal digital assistants, cellular telephones, smartphones, laptops, desktops, and other similar computing devices.

The network 110 may be a distributed network that is spread over different networks. This provides a single data communication network, which can be managed jointly or separately by each network. Besides shared communication within the network, the distributed network often also supports distributed processing. The network 110 may be a form of digital communication network such as a telecommunication network, a local area network ("LAN"), a wide area network ("WAN"), a global area network ("GAN"), the Internet, or any combination of the foregoing. The network 110 may be secure and/or unsecure and may also include wireless and/or wired and/or optical interconnection technology.

It is to be understood that the structure of the distributed computing environment and its components, connections and relationships, and their functions, are meant to be exemplary only, and are not meant to limit implementations of the inventions described and/or claimed in this document. In one example, the distributed computing environment 100 may include more, fewer, or different components. In another example, some or all of the portions of the distributed computing environment 100 may be combined into a single portion or all of the portions of the system 130 may be separated into two or more distinct portions.

FIG. 1B illustrates an exemplary component-level structure of the system 130, in accordance with an embodiment of the invention. As shown in FIG. 1B, the system 130 may include a processor 102, memory 104, input/output (I/O) device 116, and a storage device 110. The system 130 may also include a high-speed interface 108 connecting to the memory 104, and a low-speed interface 112 connecting to low speed bus 114 and storage device 110. Each of the components 102, 104, 108, 110, and 112 may be operatively coupled to one another using various buses and may be mounted on a common motherboard or in other manners as appropriate. As described herein, the processor 102 may include a number of subsystems to execute the portions of processes described herein. Each subsystem may be a self-contained component of a larger system (e.g., system 130) and capable of being configured to execute specialized processes as part of the larger system.

The processor 102 can process instructions, such as instructions of an application that may perform the functions disclosed herein. These instructions may be stored in the memory 104 or on the storage device 110, for execution within the system 130 using any subsystems described herein. It is to be understood that the system 130 may use, as appropriate, multiple processors, along with multiple memories, and/or I/O devices, to execute the processes described herein.

The memory 104 stores information within the system 130. In one implementation, the memory 104 is a volatile memory unit or units, such as volatile random access memory (RAM) having a cache area for the temporary storage of information, such as a command, a current operating state of the distributed computing environment 100, an intended operating state of the distributed computing environment 100, instructions related to various methods and/or functionalities described herein, and/or the like. In another implementation, the memory 104 is a non-volatile memory unit or units. The memory 104 may also be another form of computer-readable medium, such as a magnetic or optical disk, which may be embedded and/or may be removable. The non-volatile memory may additionally or alternatively include an EEPROM, flash memory, and/or the like for storage of information such as instructions and/or data that may be read during execution of computer instructions. The memory 104 may store, recall, receive, transmit, and/or access various files and/or information used by the system 130 during operation.

The storage device 106 is capable of providing mass storage for the system 130. In one aspect, the storage device 106 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described above. The information carrier may be a non-transitory computer- or machine-readable storage medium, such as the memory 104, the storage device 104, or memory on processor 102.

The high-speed interface 108 manages bandwidth-intensive operations for the system 130, while the low speed controller 112 manages lower bandwidth-intensive operations. Such allocation of functions is exemplary only. In some embodiments, the high-speed interface 108 is coupled to memory 104, input/output (I/O) device 116 (e.g., through a graphics processor or accelerator), and to high-speed expansion ports 111, which may accept various expansion cards (not shown). In such an implementation, low-speed controller 112 is coupled to storage device 106 and low-speed expansion port 114. The low-speed expansion port 114, which may include various communication ports (e.g., USB, Bluetooth, Ethernet, wireless Ethernet), may be coupled to one or more input/output devices, such as a keyboard, a pointing device, a scanner, or a networking device such as a switch or router, e.g., through a network adapter.

The system 130 may be implemented in a number of different forms. For example, it may be implemented as a standard server, or multiple times in a group of such servers. Additionally, the system 130 may also be implemented as part of a rack server system or a personal computer such as a laptop computer. Alternatively, components from system 130 may be combined with one or more other same or similar systems and an entire system 130 may be made up of multiple computing devices communicating with each other.

FIG. 1C illustrates an exemplary component-level structure of the client device(s) 140, in accordance with an embodiment of the invention. As shown in FIG. 1C, the client device(s) 140 includes a processor 152, memory 154, an input/output device such as a display 156, a communication interface 158, and a transceiver 160, among other components. The client device(s) 140 may also be provided with a storage device, such as a micro-drive or other device, to provide additional storage. Each of the components 152, 154, 158, and 160, are interconnected using various buses, and several of the components may be mounted on a common motherboard or in other manners as appropriate.

The processor 152 is configured to execute instructions within the client device(s) 140, including instructions stored in the memory 154, which in one embodiment includes the instructions of an application that may perform the functions disclosed herein, including certain logic, data processing, and data storing functions. The processor may be implemented as a chipset of chips that include separate and multiple analog and digital processors. The processor may be configured to provide, for example, for coordination of the other components of the client device(s) 140, such as control of user interfaces, applications run by client device(s) 140, and wireless communication by client device(s) 140.

The processor 152 may be configured to communicate with the user through control interface 164 and display interface 166 coupled to a display 156. The display 156 may be, for example, a TFT LCD (Thin-Film-Transistor Liquid Crystal Display) or an OLED (Organic Light Emitting Diode) display, or other appropriate display technology. The display interface 156 may comprise appropriate circuitry and configured for driving the display 156 to present graphical and other information to a user. The control interface 164 may receive commands from a user and convert them for submission to the processor 152. In addition, an external interface 168 may be provided in communication with processor 152, so as to enable near area communication of client device(s) 140 with other devices. External interface 168 may provide, for example, for wired communication in some implementations, or for wireless communication in other implementations, and multiple interfaces may also be used.

The memory 154 stores information within the client device(s) 140. The memory 154 can be implemented as one or more of a computer-readable medium or media, a volatile memory unit or units, or a non-volatile memory unit or units. Expansion memory may also be provided and connected to client device(s) 140 through an expansion interface (not shown), which may include, for example, a SIMM (Single In Line Memory Module) card interface. Such expansion memory may provide extra storage space for client device(s) 140 or may also store applications or other information therein. In some embodiments, expansion memory may include instructions to carry out or supplement the processes described above and may include secure information also. For example, expansion memory may be provided as a security module for client device(s) 140 and may be programmed with instructions that permit secure use of client device(s) 140. In addition, secure applications may be provided via the SIMM cards, along with additional information, such as placing identifying information on the SIMM card in a non-hackable manner.

The memory 154 may include, for example, flash memory and/or NVRAM memory. In one aspect, a computer program product is tangibly embodied in an information carrier. The computer program product contains instructions that, when executed, perform one or more methods, such as those described herein. The information carrier is a computer-or machine-readable medium, such as the memory 154, expansion memory, memory on processor 152, or a propagated signal that may be received, for example, over transceiver 160 or external interface 168.

In some embodiments, the user may use the client device(s) 140 to transmit and/or receive information or commands to and from the system 130 via the network 110. Any communication between the system 130 and the client device(s) 140 may be subject to an authentication protocol allowing the system 130 to maintain security by permitting only authenticated users (or processes) to access the protected resources of the system 130, which may include servers, databases, applications, and/or any of the components described herein. To this end, the system 130 may trigger an authentication subsystem that may require the user (or process) to provide authentication credentials to determine whether the user (or process) is eligible to access the protected resources. Once the authentication credentials are validated and the user (or process) is authenticated, the authentication subsystem may provide the user (or process) with permissioned access to the protected resources. Similarly, the client device(s) 140 may provide the system 130 (or other client devices) permissioned access to the protected resources of the client device(s) 140, which may include a GPS device, an image capturing component (e.g., camera), a microphone, and/or a speaker.

The client device(s) 140 may communicate with the system 130 through communication interface 158, which may include digital signal processing circuitry where necessary. Communication interface 158 may provide for communications under various modes or protocols, such as the Internet Protocol (IP) suite (commonly known as TCP/IP). Protocols in the IP suite define end-to-end data handling methods for everything from packetizing, addressing and routing, to receiving. Broken down into layers, the IP suite includes the link layer, containing communication methods for data that remains within a single network segment (link); the Internet layer, providing internetworking between independent networks; the transport layer, handling host-to-host communication; and the application layer, providing process-to-process data exchange for applications. Each layer contains a stack of protocols used for communications. In addition, the communication interface 158 may provide for communications under various telecommunications standards (2G, 3G, 4G, 5G, and/or the like) using their respective layered protocol stacks. These communications may occur through a transceiver 160, such as radio-frequency transceiver. In addition, short-range communication may occur, such as using a Bluetooth, Wi-Fi, or other such transceiver (not shown). In addition, GPS (Global Positioning System) receiver module 170 may provide additional navigation—and location-related wireless data to client device(s) 140, which may be used as appropriate by applications running thereon, and in some embodiments, one or more applications operating on the system 130.

The client device(s) 140 may also communicate audibly using audio codec 162, which may receive spoken information from a user and convert it to usable digital information. Audio codec 162 may likewise generate audible sound for a user, such as through a speaker, e.g., in a handset of client device(s) 140. Such sound may include sound from voice telephone calls, may include recorded sound (e.g., voice messages, music files, etc.) and may also include sound generated by one or more applications operating on the client device(s) 140, and in some embodiments, one or more applications operating on the system 130.

Various implementations of the distributed computing environment 100, including the system 130 and client device(s) 140, and techniques described here can be realized in digital electronic circuitry, integrated circuitry, specially designed ASICs (application specific integrated circuits), computer hardware, firmware, software, and/or combinations thereof.

FIG. 2 illustrates an exemplary process flow for determining a drug shortage, in accordance with an embodiment of the disclosure. In some embodiments, a system (e.g., similar to one or more of the systems described herein with respect to FIGS. 1A-1C) may perform one or more of the steps of process flow 200. For example, a drug shortage system (e.g., the system 130 described herein with respect to FIGS. 1A-1C) may perform the steps of process 200.

As shown in block 202, the process flow 200 may include the step of identifying at least one drug identifier. By way of non-limiting example, the drug shortage system may identify at least one drug identifier from at least one of a resource statement, such as an invoice comprising the at least one drug identifier, a backlog order (i.e., a backorder log), a fulfillment order log (i.e., comprising the orders that have been filled by a seller, but may comprise a quantity of drug(s) that has not been completely fulfilled and/or a quantity that is missing/unfulfilled due to a current shortage and/or backorder), and/or the like. By way of non-limiting example, the drug shortage system may identify the at least one drug identifier from a resource statement such as those described above based on receiving at least one resource statement from a third party provider (e.g., such as the seller and/or manufacturer of the drug associated with the drug identifier, a third party tracker of each of the drugs, a third party tracker of the ingredients of the drugs associated with the at least one drug, and/or the like). Further, and in some embodiments, the drug shortage system may identify each of the drugs and associated drug identifiers listed on each resource statement received by the drug shortage system. In this manner, the drug shortage system may identify all the drug identifiers for all the drugs in market for one buyer entity (e.g., a hospital, medical office, and/or the like), a plurality of buyer entities, and/or the like, based on the resource statement(s) such that the drug shortage system can identify overall drug shortages for all drugs.

As used herein, the term "drug" may refer to a prescription medication, a non-prescription medication (e.g., over-the-counter medication and/or the like), herbal medicine, antibiotic, a pharmaceutical resource, and/or the like. Similarly, the term "drug identifier" may refer to a drug name, a unique combination or sequence of alphanumeric characters (such as a national drug code (NDC), a recipient identifier—such as from a hospital, doctor's office, pharmaceutical company, and/or the like) used to uniquely identify the drug by the drug shortage system.

In some embodiments, the drug identifier and associated drug may comprise an attribute showing the drug identifier is at least one of a generic or brand-name drug. In some embodiments, the drug identifier may comprise a unique string of alphanumeric characters, binary string, and/or the like to identify the drug and whether it is a generic form and/or a brand-name form.

As shown in block 204, the process flow 200 may include the step of identifying at least one route type for the at least one drug identifier. In some embodiments, the drug shortage system may identify the at least one route type for the at least one drug identifier, whereby the route type may comprise the path the drug takes to enter the recipient's body. For instance, a route type may comprise at least one of an injection route, an oral route, a topical route, an intravenous route, an intramuscular route, a subcutaneous route, a rectal route, a vaginal route, an inhaled route, an ocular route, an optic route, and/or the like. Further and in some embodiments, the drug shortage system may identify the route type through a particular route type identifier comprised in the data associated with the drug identifier (e.g., a route type identifier and/or a plurality of potential route types where the drug may enter a recipient's body in a plurality of paths such as injection, oral, rectal, vaginal, and/or the like). Thus, and in some embodiments, the drug identifier may be associated with a single route type and/or a plurality of route types.

In some embodiments, the drug shortage system may separate each drug identifier to only be associated with a singular route type to determine the prediction shortage for the specific drug and specific route type. Thus, and in some embodiments like those described herein, the drug shortage system may determine the prediction shortages for each drug associated with each drug's associated route types, individually and/or together. For instance, the drug shortage system may sort the drug identifiers based on route type, such that the listing of the drug identifiers that may be in shortage and/or may be in shortage at a future period are separated based on each route type. Such a sorting by route type for drug shortages is described in further detail below with respect to FIG. 5.

As shown in block 206, the process flow 200 may include the step of determining at least one feature type associated with the at least one drug identifier, wherein each feature type comprises at least one attribute. In some embodiments, the drug shortage system may determine at least one feature type for each drug identifier identified by the drug shortage system. For instance, the feature types may comprise features of the drug such as but not limited to fixed drug feature(s), shortage event feature(s), changing drug feature(s), invoice/line item feature(s), relatedness feature(s), and/or the like. In some embodiments, each feature type may comprise at least one attribute, such as a question which seeks an answer about the drug in a quantitative or numerical form. Such an attribute may then be used to generate a shortage score for each feature type.

For instance, the fixed drug feature(s) may indicate the drug's attributes which may not change with time and may be used to identify the same drug across different/multiple dimensions (e.g., different route types, different resource statements, different regions, and/or the like). In some embodiments, the fixed drug feature(s) may comprise at least one quantitative analysis question (i.e., at least one attribute) such as but not limited to "is the average contracted invoice price less than a certain amount (e.g., three dollars, four dollars, five dollars, and/or the like)," "is the drug injectable," "is the drug generic," "are there less than three manufacturers or supplier entities," "is there only one manufacturer/supplier," "are there more than ten manufacturers or suppliers," "is the drug a controlled substance," "are all active pharmaceutical ingredients (API) manufacturers or suppliers in the same city, state, or country," "are all finished goods manufacturers or suppliers in the same city, state, or country," and/or the like. Thus, and by way of non-limiting example, the fixed drug feature(s) and its associated quantitative analysis questions (i.e., attributes)

may be used to generate a numerical value for the fixed drug feature(s) for the drug identifier(s).

Additionally, the shortage event feature(s) may indicate the attributes that describe historical and/or current shortage details of the drug(s) in a quantitative form. For instance and in some embodiments, the shortage event feature(s) may comprise at least one quantitative analysis question (i.e., at least one attribute) such as but not limited to "is there any history of a shortage," "how many times has the drug been under shortage in the past," "how long was the most recent shortage" "is the drug under a current, official shortage," "how long since the start of said current shortage," and/or the like. Thus, and by way of non-limiting example, the shortage event feature(s) and its associated quantitative analysis questions may be used to generate a numerical value for the shortage event feature(s) for the drug identifier(s).

The changing drug feature(s) may indicate the attributes that vary over time, reveal more market dynamic influences for a given drug, readily identify broad supply issues, and/or the like. For instance and in some embodiments, the changing drug feature(s) may comprise at least one quantitative analysis question (i.e., at least one attribute) such as but not limited to "are any national drug codes (NDCs) (e.g., drug identifiers created by the federal drug administration (FDA)) under current and/or active FDA recall," "are all dosage forms experiencing 'similar' trends (e.g., are all route types experiencing similar trends and/or are all dosage amounts experiencing similar trends)," "are all wholesalers experiencing 'similar' trends," "are all distribution centers (DCs) experiencing 'similar' trends," "has the drug appeared on a recent manufacturer/supplier backorder report," and/or the like. Thus, and by way of non-limiting example, the changing drug feature(s) and its associated quantitative analysis questions may be used to generate a numerical value for the changing drug feature(s) for the drug identifier(s).

Additionally, the invoice/line-item feature(s) may indicate the attributes that describe details of supply across the membership, broad, market-level information helping to pinpoint location of disruption (i.e., upstream, downstream, and/or the like). For instance and in some embodiments, the changing drug feature(s) may comprise at least one quantitative analysis question (i.e., at least one attribute) such as but not limited to "has the fill rate declined at least eight of the last ten days," "has the fill rate declined below the past annual average," "has the fill rate dropped 20-25% compared to a recent baseline for the drug," "has there been at least five manufacturer-related invoice issues in the last ten days," and/or the like. Thus, and by way of non-limiting example, the invoice/line item feature(s) and its associated quantitative analysis questions/answers may be used to generate a numerical value for all the feature(s) to generate the shortage score(s) for the drug identifier(s).

The relatedness feature(s) may indicate the attributes to describe patterns within drug equivalents and alternatives (i.e., trends across related drugs/products). Thus, and in some embodiments, the related feature(s) may comprise alternative feature(s) and/or equivalent feature(s), whereby each of the alternative feature(s) and/or equivalent feature(s) may comprise at least one quantitative analysis question (i.e., at least one attribute) which may be used to generate a numerical value for each of the alternative feature(s) and/or equivalent feature(s). Thus, and by way of non-limiting example, the relatedness feature(s) and its associated quantitative analysis questions may be used to generate a numerical value for the relatedness feature(s) for the drug identifier(s).

In some embodiments, the alternative feature(s) may comprise at least one quantitative analysis question (i.e., at least one attribute) such as but not limited to "average number of days of declining fill rate within the last ten days, for alternative drugs," "average ten-day rolling average fill rate, for alternative drugs," "average number of days the fill rate has declined at least eight of the last ten days, for alternative drugs," "average number of days the fill rate has been lower in the last ten days compared to everything prior to the last ten days, for alternative drugs," "average number of days the fill rate has declined 20-25% in the last ten days, for alternative drugs," and/or the like). As used herein, the term "alternative drugs" may refer to drugs that comprise the same or similar capabilities as the particular drug associated with the drug identifier for which the features are intended to describe but do not comprise the exact ingredients or makeup/value of ingredients, which may be used alternatively to the drug associated with the drug identifier.

In some embodiments, the equivalent feature(s) may comprise at least one quantitative analysis question (i.e., at least one attribute) such as but not limited to "average number of days of declining fill rate within the last ten days, for equivalent drugs," "average ten-day rolling average fill rate, for equivalent drugs," "average number of days the fill rate has declined at least eight of the last ten days, for equivalent drugs," "average number of days the fill rate has been lower in the last ten days compared to everything prior to the last ten days, for equivalent drugs," "average number of days the fill rate has declined 20-25% in the last ten days, for equivalent drugs," and/or the like. As used herein, the term "equivalent drug" may refer to drugs that comprise the same or similar capabilities as the particular drug associated with the drug identifier for which the features are intended to describe and comprise the exact ingredients and makeup/value of ingredients, which may be used as an equivalent to the drug associated with the drug identifier.

As shown in block 208, the process flow 200 may include the step of generating a shortage score for the drug identifier. In some embodiments, the drug shortage system may generate an overall shortage score of the drug identifier based on each of the attributes for each of the feature types(s), whereby the numerical values for each of the attributes may be used to generate the shortage score. For instance, and in some embodiments, the shortage score may be an aggregate of the attributes and associated numerical values from all the feature types, such that the shortage score is an overall total of the attribute numerical answers for each of the feature types. In some embodiments, the shortage score may be generated by a model, such as the drug shortage model described in more detail below with respect to FIG. 3.

As shown in block 210, the process flow 200 may include the step of applying a post-score change to the shortage score, wherein the post-score change is based on at least one supplemental feature. By way of non-limiting example, the drug shortage system may apply a post-score change to the shortage score such that the post-score change is used to refine the shortage score based on supplemental features associated with the current shortage score, previous shortage scores/shortages, route types, fulfillment orders, and/or the like. For instance, such a post-score change may comprise any one of the following supplemental features and associated post-score change to the shortage score.

| SUPPLEMENTAL FEATURES | POST-SCORE CHANGE |
|---|---|
| Score Increased | +1 |
| Score Increased<br>In Current Shortage | −1 |
| Score Increased<br>Not In Current Shortage | +2 |
| Score Increased<br>Not In Current Shortage<br>Injectable Route Type | +3 |
| Score Increased<br>Not In Current Shortage<br>Injectable Route Type<br>Increased Proportion of Missing Units | +4 |
| Score Increased<br>Not In Current Shortage<br>Injectable Route Type<br>Newly Appeared on Backorder Report | +5 |

For instance, and in some embodiments, the post-score change may be based on supplemental features such as but not limited to at least one of a previous supply trend for the drug identifier (e.g., score increased, score decreased, and/or the like), a current supply trend (e.g., not in current shortage or in current shortage), the route type (e.g., injectable route type, and/or the like), a supply trend of units (e.g., increased proportion of missing units, and/or the like), a backorder trend (e.g., newly appeared on backorder report), and/or the like. Additionally, and based on these supplemental features, the shortage score may be changed by the post-score change (e.g., add one, minus one, add two, add three, add four, add five, and/or the like, to the shortage score). In some embodiments, each of the supplemental features and associated post-score change(s) may be determined by a model, such as the drug shortage model described in more detail below with respect to FIG. 3 and applied, by the model, to the shortage score. Further, and based on the shortage score and post-score change, a drug shortage score may be generated.

As shown in block 212, the process flow 200 may include the step of generating a drug shortage score based on the post-score change applied to the shortage score. By way of non-limiting example, the drug shortage system may generate a drug shortage score by applying a post-score change to the shortage score, such that the drug shortage score is an overall determination of a likelihood a drug associated with the drug identifier will go into shortage at a current period and/or a future period.

In some embodiments, the drug shortage and the processes described herein to generate the drug shortage score may be generated at a weekly rate. In some embodiments, the drug shortage and the processes described herein to generate the drug shortage score may be generated at a daily rate, bi-weekly rate, monthly rate, and/or the like. Such a generation rate of the drug shortage score may be determined by the drug shortage system itself, by the drug shortage model, by a manager of the drug shortage system, by a client of the drug shortage system (e.g., a buyer of drugs), and/or the like.

FIG. 3 illustrates an exemplary process flow for generating a shortage score, in accordance with an embodiment of the disclosure. In some embodiments, a system (e.g., similar to one or more of the systems described herein with respect to FIGS. 1A-1C) may perform one or more of the steps of process flow 300. For example, a drug shortage system (e.g., the system 130 described herein with respect to FIGS. 1A-1C) may perform the steps of process 300.

In some embodiments and as shown in block 302, the process flow 300 may include the step of identifying data associated with the at least one drug identifier from at least one resource statement. By way of non-limiting example, the drug shortage system may identify data associated with the at least one drug identifier (and other such drug identifiers associated with the drug shortage system, such as the drug identifiers identified from the resource statement(s)), such as data from previous resource statements, data of previous shortages for the drug identifier(s), data of the route types for each drug identifier, data of whether each drug identifier is generic or name-brand, data of manufacturers/suppliers, and/or the like.

In some embodiments and as shown in block 304, the process flow 300 may include the step of applying a drug shortage model to the data associated with the at least one drug identifier. As used herein, the term drug shortage model may refer to at least one of a linear heuristic model, which may be configured to determine and/or generate a drug shortage score. Such a linear heuristic model may be configured to determine the weight to assign to each feature and/or attribute of the feature type(s) as well as the score (e.g., value) each feature type's attributes will comprise.

By way of non-limiting example, the drug shortage system may apply the drug shortage model to the data identified and associated with each of the drug identifier(s). Such an application of this data to the drug shortage model may be used to train the drug shortage model on historical and current data for each of the drug identifiers.

In some embodiments and as shown in block 306, the process flow 300 may include the step of determining, based on the drug shortage model, the at least one feature type. In some embodiments and based on at least the data identified, the drug shortage model may determine the at least one feature type for the drug identifier and the associated shortage score based on the feature type(s). In this manner, the drug shortage model may determine which feature types should be considered to generate the drug shortage score as well as the attributes that will be considered for each feature type.

In some embodiments and as shown in block 308, the process flow 300 may include the step of generating, based on the drug shortage model, the drug shortage score. By way of non-limiting example, the drug shortage system (using the drug shortage model) may generate the numerical value for the feature type(s) based on the at least one attribute for each feature type. In some embodiments, the drug shortage model may weigh the attributes equally for each feature type in order to generate the numerical value and the associated shortage score, which is based on the aggregation of the numerical values of for the feature type attribute(s), based on the feature type. In some embodiments, and based on the drug shortage model, the drug shortage model may weigh each attribute at different values in order to determine which attributes should be considered more heavily to generate the most accurate drug shortage score. For instance, and where the route type for a drug identifier is an injection route, the drug shortage model may determine this attribute should be weighed more heavily to determine that the prediction shortage will likely be higher as compared to the situation where the route type may be an oral route.

In some embodiments, the drug shortage model may receive feedback indicators from at least one of a client of the drug shortage system, a manager of the drug shortage system, and/or the like. In this manner, the drug shortage model may further be trained after generating the drug shortage scores. For example, a drug shortage system (e.g., the system 130 described herein with respect to FIGS. 1A-1C) may perform the steps of process 400.

FIG. 4 illustrates an exemplary process flow for determining a route type for the drug identifier(s) and using the route type to generate the shortage score for each drug identifier, in accordance with an embodiment of the disclosure. In some embodiments, a system (e.g., similar to one or more of the systems described herein with respect to FIGS. 1A-1C) may perform one or more of the steps of process flow 400.

In some embodiments and as shown in block 402, the process flow 400 may include the step of determining a route type from the at least one route type for the at least one drug identifier, wherein the route type is used to generate the shortage score for the drug identifier. In some embodiments, the process described in block 502 may precede the process described in block 214, as detailed above. By way of non-limiting example, the drug shortage system may determine a route type (based on each of the potential route types described herein and/or the like) for each drug associated with each drug identifier considered by the drug shortage system. For instance, the drug shortage system may determine a route type—and/or a plurality of route types—for each drug identifier based on the data for the associated drug. Such drug data may comprise all the ways the drug may enter a recipient's system (e.g., their body, which may comprise an injection route, an oral route, an optical route, and/or the like). Based on this determined route type(s), the drug shortage system may sort the drug identifiers for each route type, such that there may be multiple copies of the same drug identifiers for different route type listings (e.g., where the drug may be ingested, injected, and/or the like) and/or such that a unique drug identifier is used for each route type (e.g., a unique drug identifier is used to identify the same drug for each route type).

Further, and in some embodiments, the drug shortage system may determine, the shortage score, and the drug shortage score based on the particular route type sorted by the drug shortage system. In this manner, the drug shortage system may sort all the drug identifiers into listings with other drug identifiers of the same route type, such that the route type is used to determine which drug identifiers are more likely to go into shortage.

FIG. 5 illustrates an exemplary process flow for generating a drug-route shortage graphical user interface, in accordance with an embodiment of the disclosure. In some embodiments, a system (e.g., similar to one or more of the systems described herein with respect to FIGS. 1A-1C) may perform one or more of the steps of process flow 500. For example, a drug shortage system (e.g., the system 130 described herein with respect to FIGS. 1A-1C) may perform the steps of process 500.

In some embodiments and as shown in block 502, the process flow 500 may include the step of ranking each drug shortage score for each drug identifier in a route-type rank, wherein the route-type rank comprises the drug shortage score for each drug identifier associated with a same route type. In some embodiments, the process described herein with respect to FIG. 5 may follow block 214 of FIG. 2. By way of non-limiting example, the drug shortage system may rank each drug shortage score generated by the drug shortage system for each drug identifier identified by the drug shortage system in a route-type rank, such that each route type is associated with a listing of drug shortage scores for each drug of the route type. For instance, and whereby a route type is associated with a plurality of drug identifiers (e.g., a plurality of drugs use an injection route type), the drug shortage system may generate a route-type list of all the drug identifiers associated with the route type based on their drug shortage scores. In some embodiments, the drug identifiers and drug shortage scores may be ranked from highest drug shortage score (e.g., indicating a higher likelihood the drug is in shortage or will go into shortage) to lowest drug shortage score (e.g., indicating a lower likelihood the drug is in shortage or will go into shortage) for each route type, individually.

In some embodiments and as shown in block 504, the process flow 500 may include the step of generating a drug-route shortage graphical user interface wherein the drug-route shortage graphical user interface comprises the at least one drug shortage score of a route-type that meets a drug-route shortage threshold. By way of non-limiting example, the drug shortage system may generate a drug-route shortage graphical user interface which comprises the drug shortage scores and associated drug identifiers which meet the drug-route shortage threshold, whereby the drug-route shortage threshold dynamically changes based on the drug identifiers in each route type. The drug-route shortage threshold's score may change in accordance with exemplary blocks 506 and 508. Thus, and in some embodiments, the drug-route shortage graphical user interface may only show the drug identifiers and associated top drug shortage scores for each route type.

In some embodiments and as shown in block 506, the process flow 500 may include the step of generating, in an instance where the route-type is less than the drug-route shortage threshold, the drug-route shortage graphical user interface to indicate a pre-determined percentage of a top drug shortage scores. By way of non-limiting example, the drug shortage system may generate the drug-route shortage graphical user interface to indicate and/or show the drug identifiers and associated drug shortage scores which meet a pre-determined percentage of the top drug shortage scores. In some embodiments, the pre-determined percentage may be pre-determined by a client of the drug shortage system, by a manager of the drug shortage system, and/or by the drug shortage system itself (e.g., by the drug shortage model), and/or the like.

In some embodiments, the pre-determined percentage may comprise a percentage of a top 15%, a top 20%, a top 25%, a top 30%, a top 35%, a top 40%, a top 45%, a top 50%, and/or the like. For instance, and where the pre-determined percentage is determined to be the top 15% of the top prediction shortage scores and associated predication identifiers and the drug-route shortage threshold is set to a particular number (e.g., 200, which is similar to the example provided below), the drug shortage system may generate the drug-route shortage graphical user interface to indicate/show the top 15% drug shortage scores and associated drug identifiers when the route type does not comprise at least 200 drugs/drug identifiers.

In some embodiments and as shown in block 508, the process flow 500 may include the step of generating, in an instance where the route-type meets the drug-route shortage threshold, the drug-route shortage graphical user interface to indicate the drug-route shortage threshold of the top drug shortage scores. By way of non-limiting example, the drug shortage system may generate the drug-route shortage graphical user interface to indicate and/or show the drug identifiers and associated drug shortage scores which meet a pre-determined shortage threshold of the top drug shortage scores. In some embodiments, the pre-determined shortage threshold may be pre-determined by a client of the drug shortage system, by a manager of the drug shortage system, and/or by the drug shortage system itself (e.g., by the percentage shortage model), and/or the like.

In some embodiments, the pre-determined shortage threshold may comprise the top 200 drug shortage scores and associated drug identifiers for each route type. For instance, and where a route type comprises 500 drug identifiers, the drug-route graphical shortage graphical user interface may comprise only the top 200 drug shortage scores and associated drug identifiers for the route type.

FIG. 6 illustrates an exemplary process flow for generating the shortage score, in accordance with an embodiment of the disclosure. In some embodiments, a system (e.g., similar to one or more of the systems described herein with respect to FIGS. 1A-1C) may perform one or more of the steps of process flow 600. For example, a drug shortage system (e.g., the system 130 described herein with respect to FIGS. 1A-1C) may perform the steps of process 600.

In some embodiments and shown in block 602, the process flow 600 may include the step of identifying data associated with the at least one drug identifier from at least one resource statement. In some embodiments, the process described herein with respect to FIG. 6 may follow the process described with respect to block 202. By way of non-limiting example, the drug shortage system may identify data associated with the at least one drug identifier from at least one resource statement by parsing the data of each resource statement received and/or identified by the drug shortage system to determine at least one of the drugs, drug identifiers, units, unit values (e.g., cost per unit), back-order data (e.g., whether any drugs are back-ordered), whether the drug is generic and/or name-brand, route type, manufacturer, supplier, controlled substance indictor, and/or the like. Such data may additionally comprise any of the data herein described for use in determining the attributes for the feature types.

In some embodiments and as shown in block 604, the process flow 600 may include the step of filtering the data associated with the at least one drug identifier to generate filtered drug data of the at least one drug identifier. By way of non-limiting example, the drug shortage system may filter the parsed data associated with each drug identifier from the resource statements to generate filtered drug data. In this manner, the filtered drug data may be cleaned to filter out data, such as the data that does not comprise a national drug code (e.g., which may indicate or represent non-drug items or erroneous, duplicated, or returned resource transactions), the data that comprises a "0" (zero) quantity ordered (e.g., which may indicate split order items, where part of the resource order was shipped after the original order and where the recipient paid the invoice already), data that comprises weekend invoice data (e.g., which may indicate irregular transactions that are inconsistent between members/recipients and hospitals), data that comprises negative values (e.g., negative total spent, negative quantity ordered, negative total units, and/or the like), data that comprises pharmacy items with no invoice history in the last 45 days and/or another such predetermined historical period (e.g., allows the identification of more recent and frequently ordered items/drugs and filter out less important or impactful purchases), and/or the like.

In some embodiments and as shown in block 606, the process flow 600 may include the step of applying the filtered drug data to the at least one attribute of each feature type to generate the shortage score. By way of non-limiting example, the drug shortage system may apply the filtered drug data to at least one attribute from the feature type(s), whereby the filtered data may be used for the attributes to generate the numerical output of the feature types and associated shortage score.

As will be appreciated by one of ordinary skill in the art, the present invention may be embodied as an apparatus (including, for example, a system, a machine, a device, a computer program product, and/or the like), as a method (including, for example, a business process, a computer-implemented process, and/or the like), or as any combination of the foregoing. Accordingly, embodiments of the present invention may take the form of an entirely software embodiment (including firmware, resident software, micro-code, and the like), an entirely hardware embodiment, or an embodiment combining software and hardware aspects that may generally be referred to herein as a "system." Furthermore, embodiments of the present invention may take the form of a computer program product that includes a computer-readable storage medium having computer-executable program code portions stored therein.

As the phrase is used herein, a processor may be "configured to" perform a certain function in a variety of ways, including, for example, by having one or more general-purpose circuits perform the function by executing particular computer-executable program code embodied in computer-readable medium, and/or by having one or more application-specific circuits perform the function.

It will be understood that any suitable computer-readable medium may be utilized. The computer-readable medium may include, but is not limited to, a non-transitory computer-readable medium, such as a tangible electronic, magnetic, optical, infrared, electromagnetic, and/or semiconductor system, apparatus, and/or device. For example, in some embodiments, the non-transitory computer-readable medium includes a tangible medium such as a portable computer diskette, a hard disk, a random access memory (RAM), a read-only memory (ROM), an erasable programmable read-only memory (EPROM or Flash memory), a compact disc read-only memory (CD-ROM), and/or some other tangible optical and/or magnetic storage device. In other embodiments of the present invention, however, the computer-readable medium may be transitory, such as a propagation signal including computer-executable program code portions embodied therein.

It will also be understood that one or more computer-executable program code portions for carrying out the specialized operations of the present invention may be required on the specialized computer include object-oriented, scripted, and/or unscripted programming languages, such as, for example, Java, Perl, Smalltalk, C++, SAS, SQL, Python, Objective C, and/or the like. In some embodiments, the one or more computer-executable program code portions for carrying out operations of embodiments of the present invention are written in conventional procedural programming languages, such as the "C" programming languages and/or similar programming languages. The computer program code may alternatively or additionally be written in one or more multi-paradigm programming languages, such as, for example, F#.

Embodiments of the present invention are described above with reference to flowcharts and/or block diagrams. It will be understood that steps of the processes described herein may be performed in orders different than those illustrated in the flowcharts. In other words, the processes represented by the blocks of a flowchart may, in some embodiments, be in performed in an order other that the order illustrated, may be combined or divided, or may be performed simultaneously. It will also be understood that the blocks of the block diagrams illustrated, in some embodiments, merely conceptual delineations between systems and one or more of the systems illustrated by a block in the block diagrams may be combined or share hardware and/or software with another one or more of the systems illustrated by a block in the block diagrams. Likewise, a device, system, apparatus, and/or the like may be made up of one or more devices, systems, apparatuses, and/or the like. For example, where a processor is illustrated or described herein, the processor may be made up of a plurality of microprocessors or other processing devices which may or may not be coupled to one another. Likewise, where a memory is illustrated or described herein, the memory may be made up of a plurality of memory devices which may or may not be coupled to one another.

It will also be understood that the one or more computer-executable program code portions may be stored in a transitory or non-transitory computer-readable medium (e.g., a memory, and the like) that can direct a computer and/or other programmable data processing apparatus to function in a particular manner, such that the computer-executable program code portions stored in the computer-readable medium produce an article of manufacture, including instruction mechanisms which implement the steps and/or functions specified in the flowchart(s) and/or block diagram block(s). The computer program product comprises a non-transitory computer-readable storage medium having computer-executable instructions.

The one or more computer-executable program code portions may also be loaded onto a computer and/or other programmable data processing apparatus to cause a series of operational steps to be performed on the computer and/or other programmable apparatus. In some embodiments, this produces a computer-implemented process such that the one or more computer-executable program code portions which execute on the computer and/or other programmable apparatus provide operational steps to implement the steps specified in the flowchart(s) and/or the functions specified in the block diagram block(s). Alternatively, computer-implemented steps may be combined with operator and/or human-implemented steps in order to carry out an embodiment of the present invention.

Many alterations and modifications may be made by those having ordinary skill in the art without departing from the spirit and scope of the disclosed embodiments. Therefore, it must be understood that the illustrated embodiments have been set forth only for the purposes of example and that it should not be taken as limiting the embodiments as defined by the following claims. For example, notwithstanding the fact that the elements of a claim are set forth below in a certain combination, it must be expressly understood that the embodiment includes other combinations of fewer, more or different elements, which are disclosed herein even when not initially claimed in such combinations.

Thus, specific embodiments and applications of a method for using a machine learning algorithm and a natural language processing to categorize service suppliers have been disclosed. It should be apparent, however, to those skilled in the art that many more modifications besides those already described are possible without departing from the disclosed concepts herein. The disclosed embodiments, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Insubstantial changes from the claimed subject matter as viewed by a person with ordinary skill in the art, now known or later devised, are expressly contemplated as being equivalent within the scope of the claims. Therefore, obvious substitutions now or later known to one with ordinary skill in the art are defined to be within the scope of the defined elements. The claims are thus to be understood to include what is specifically illustrated and described above, what is conceptually equivalent, what can be obviously substituted and also what essentially incorporates the essential idea of the embodiments. In addition, where the specification and claims refer to at least one of something selected from the group consisting of A, B, C . . . and N, the text should be interpreted as requiring at least one element from the group which includes N, not A plus N, or B plus N, etc.

The words used in this specification to describe the various embodiments are to be understood not only in the sense of their commonly defined meanings, but to include by special definition in this specification structure, material or acts beyond the scope of the commonly defined meanings. Thus, if an element can be understood in the context of this specification as including more than one meaning, then its use in a claim must be understood as being generic to all possible meanings supported by the specification and by the word itself.

The definitions of the words or elements of the following claims, therefore, include not only the combination of elements which are literally set forth but all equivalent structure, material or acts for performing substantially the same function in substantially the same way to obtain substantially the same result. In this sense, it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a sub combination or variation of a sub combination.

What is claimed is:

1. A system for determining a drug shortage, the system comprising:

a memory device with computer-readable program code stored thereon;

at least one processing device operatively coupled to the memory device and at least one communication device, wherein executing the computer-readable code is configured to cause the at least one processing device to:

identify at least one drug identifier;

identify at least one route type for the at least one drug identifier;

determine at least one feature type associated with the at least one drug identifier, wherein each feature type comprises at least one attribute;

generate a shortage score for the at least one drug identifier;

apply a post-score change to the shortage score, wherein the post-score change is based on at least one supplemental feature, wherein the post-score change is applied directly to the shortage score;

generate a drug shortage score based on the post-score change applied to the shortage score; and rank each drug shortage score for each drug identifier in a route-type rank, wherein the route-type rank comprises the drug shortage score for each drug identifier associated with a same route type.

2. The system of claim 1, wherein the processing device is further configured to:

identify data associated with the at least one drug identifier from at least one resource statement;

apply a drug shortage model to the data associated with the at least one drug identifier, wherein the data comprises current data and historical data of the at least one drug identifier, and wherein applying the drug shortage model to the data trains the drug shortage model;

determine, based on the drug shortage model, the at least one feature type; and generate, based on the drug shortage model, the drug shortage score.

3. The system of claim 2, wherein the processing device is further configured to:

identify a plurality of features associated with the at least one drug identifier;

identify, for each feature of the plurality of features, at least one attribute associated with a quantitative analysis question to identify quantitative analysis questions;

generate, for each quantitative analysis question of the quantitative analysis questions, a numerical value; and generate, using the drug shortage model and based on an aggregation of the numerical values, the drug shortage score for the at least one drug identifier.

4. The system of claim 1, wherein the processing device is further configured to determine a route type from the at least one route type for the at least one drug identifier, wherein the route type is used to generate the shortage score for the drug identifier.

5. The system of claim 1, wherein the processing device is further configured to generate a drug-route shortage graphical user interface, wherein the drug-route shortage graphical user interface comprises the drug shortage scores of a route-type that meet a drug-route shortage threshold, wherein, in an instance where the route-type is less than the drug-route shortage threshold, generate the drug-route shortage graphical user interface to indicate a pre-determined percentage of a top drug shortage scores, or wherein, in an instance where the route-type meets the drug-route shortage threshold, generate the drug-route shortage graphical user interface to indicate the drug-route shortage threshold of the top drug shortage scores.

6. The system of claim 5, wherein the processing device is further configured to:

dynamically change, based on the drug identifiers in the route-type, the drug-route shortage threshold; and generate the graphical user interface based on the changed drug-route shortage threshold.

7. The system of claim 1, wherein the processing device is further configured to:

identify data associated with the at least one drug identifier from at least one resource statement;

filter the data associated with the at least one drug identifier to generate filtered drug data of the at least one drug identifier; and apply the filtered drug data to the at least one attribute of each feature type to generate the shortage score.

8. The system of claim 1, wherein the at least one route type comprises at least one of an injection route, an oral route, a topical route, an intravenous route, an intramuscular route, a subcutaneous route, a rectal route, a vaginal route, an inhaled route, an ocular route, or an optic route.

9. The system of claim 1, wherein the at least one attribute comprises at least one of a fixed drug feature, a shortage event feature, a changing drug feature, a line-item feature, or a relatedness feature.

10. The system of claim 1, wherein the shortage score is an aggregate of each attribute associated with each feature type.

11. The system of claim 1, wherein the at least one supplemental feature comprises an increase or decrease to the shortage score based on at least one of a previous supply trend for the drug identifier, a current supply trend, the route type, a supply trend of units, or a backorder trend.

12. The system of claim 1, wherein the drug shortage score is generated at a weekly rate.

13. The system of claim 1, wherein the direct application of the post-score change comprises an addition of the post-score change to the shortage score, or a subtraction of the post-score change from the shortage score.

14. A computer program product for determining a drug shortage, wherein the computer program product comprises at least one non-transitory computer-readable medium having computer-readable program code portions embodied therein, the computer-readable program code portions which when executed by a processing device are configured to cause the processor to:

identify at least one drug identifier;

identify at least one route type for the at least one drug identifier;

determine at least one feature type associated with the at least one drug identifier, wherein each feature type comprises at least one attribute;

generate a shortage score for the drug identifier;

apply a post-score change to the shortage score, wherein the post-score change is based on at least one supplemental feature, wherein the post-score change is applied directly to the shortage score;

generate a drug shortage score based on the post-score change applied to the shortage score; and rank each drug shortage score for each drug identifier in a route-type rank, wherein the route-type rank comprises the drug shortage score for each drug identifier associated with a same route type.

15. The computer program product of claim 14, wherein the processing device is further configured to cause the processor to:

identify data associated with the at least one drug identifier from at least one resource statement;

apply a drug shortage model to the data associated with the at least one drug identifier;

determine, based on the drug shortage model, the at least one feature type; and generate, based on the drug shortage model, the drug shortage score.

16. The computer program product of claim 14, wherein the processing device is further configured to cause the processor to determine a route type from the at least one route type for the at least one drug identifier, wherein the route type is used to generate the shortage score for the drug identifier.

17. The computer program product of claim 14, wherein the processing device is further configured to cause the processor to generate a drug-route shortage graphical user interface, wherein the drug-route shortage graphical user interface comprises the drug shortage scores of a route-type that meet a drug-route shortage threshold, wherein, in the instance where the route-type is less than the drug-route shortage threshold, generate the drug-route shortage graphical user interface to indicate a pre-determined percentage of a top drug shortage scores, or wherein, in an instance where the route-type meets the drug-route shortage threshold, generate the drug-route shortage graphical user interface to indicate the drug-route shortage threshold of the top drug shortage scores.

18. A computer-implemented method for determining a drug shortage, the computer-implemented method comprising:

identifying at least one drug identifier;

identifying at least one route type for the at least one drug identifier;

determining at least one feature type associated with the at least one drug identifier, wherein each feature type comprises at least one attribute;

generating a shortage score for the drug identifier;

applying a post-score change to the shortage score, wherein the post-score change is based on at least one supplemental feature, wherein the post-score change is applied directly to the shortage score;

generating a drug shortage score based on the post-score change applied to the shortage score; and ranking each drug shortage score for each drug identifier in a route-type rank, wherein the route-type rank comprises the drug shortage score for each drug identifier associated with a same route type.

19. The computer-implemented method of claim 18, further comprising determining a route type from the at least one route type for the at least one drug identifier, wherein the route type is used to generate the shortage score for the drug identifier.

20. The computer-implemented method of claim 18, further comprising ranking each drug shortage score for each drug identifier in a route-type rank, wherein the route-type rank comprises the drug shortage score for each drug identifier associated with a same route type.

* * * * *